United States Patent [19]

Nomura et al.

[11] Patent Number: 5,087,755
[45] Date of Patent: Feb. 11, 1992

[54] PROCESS FOR PRODUCING AROMATIC AMINES BY REDUCTION OF AROMATIC NITRO COMPOUNDS

[75] Inventors: Kotohiro Nomura; Masaru Ishino, both of Osaka, Japan

[73] Assignee: Sumitomo Chemical Company, Limited, Osaka, Japan

[21] Appl. No.: 436,690

[22] Filed: Nov. 15, 1989

[30] Foreign Application Priority Data

Nov. 18, 1988 [JP] Japan .................................. 63-293394
Aug. 31, 1989 [JP] Japan .................................. 1-226930

[51] Int. Cl.$^5$ .......................................... C07C 209/36
[52] U.S. Cl. .................................... 564/422; 546/171; 546/311; 548/301; 552/236; 552/238; 562/58; 564/86; 564/416; 564/417; 564/418; 564/420
[58] Field of Search ............... 564/416, 420, 417, 418, 564/422, 86; 546/171, 311; 548/301; 552/236, 238; 562/58

[56] References Cited

U.S. PATENT DOCUMENTS

| | | | |
|---|---|---|---|
| 3,293,295 | 12/1966 | Swakon et al. | 564/416 |
| 3,578,713 | 5/1971 | Scott | 564/416 |
| 3,637,820 | 1/1972 | Dodman et al. | 564/416 X |
| 3,944,615 | 3/1976 | Iqbal | 564/416 |

FOREIGN PATENT DOCUMENTS

| | | | |
|---|---|---|---|
| 0097592 | 6/1983 | European Pat. Off. | 564/416 |
| 0293999 | 12/1988 | European Pat. Off. | 564/416 |

OTHER PUBLICATIONS

"Application of the Water-Gas Shift Reaction. Reduction of Nitrobenzenes with CO and $H_2O$ Catalyzed by Ru(II) Complexes".

Tamon Okano et al, Chemistry Letters, pp. 1083-1086, 1981.
Journal of Molecular Catalysis, 5 (1979) 319-330, Robert C. Ryan et al., Jan. 18, 1978.
Journal of Molecular Catalysis, 12 (1981) 385-387, K. Kaneda et al., Jan. 5, 1981.
Tetrahedron Letters vol. 21, pp. 2603-2404 (1980), "The Ruthenium Carbonyl Catalyzed Reduction of Nitro Compounds by Phase Transfer Catalysis", Howard Alper et al.
Journal of Molecular Catalysis, 18 (1983) 113-116, Enzo Alessio et al., Jun. 28, 1982.
Chemical Abstracts, vol. 104, No. 26, Jun. 30, 1986, p. 759, Abstract No. 236073t.
Chemical Abstracts, vol. 100, No. 15, Apr. 9, 1984, p. 525, Abstract No. 120303f.

Primary Examiner—Richard L. Raymond
Attorney, Agent, or Firm—Birch, Stewart, Kolasch & Birch

[57] ABSTRACT

A process for producing an aromatic amine under moderate conditions is provided wherein a catalyst higher in activity than conventional catalysts is used. Reduction of an aromatic nitro compound under a $CO/H_2O$ system is conducted using a rhodium compound catalyst in the presence of an aqueous alkali solution such as aqueous sodium hydroxide solution. Alternatively, an aromatic nitro compound is reduced under a $CO/H_2O$ system using a rhodium compound or a ruthenium compound catalyst in the presence of the aqueous alkali solution and additionally at least one compound of amine compounds, diamine compounds, phosphine compounds, phosphite compounds, and diphosphine compounds.

35 Claims, No Drawings

PROCESS FOR PRODUCING AROMATIC AMINES BY REDUCTION OF AROMATIC NITRO COMPOUNDS

BACKGROUND OF THE INVENTION

The present invention relates to a process for producing aromatic amines by reduction of aromatic nitro compounds.

Aromatic amines including aniline are industrially important compounds used as medicines, agricultural chemicals, dyes, pigments, pharmaceuticals and intermediates thereof.

It is known to produce aromatic amines by reduction of aromatic nitro compounds under a $CO/H_2O$ system in the presence of a catalyst. U.S. Pat. No. 3,944,615 discloses to carry out the reaction in a solvent such as pyridine or N-methylpyridine using $Rh_6(CO)_{16}$ or $Rh_2O_3$ as a catalyst under high temperature and high pressure e.g. 50°-150° C. and CO 50-120 atm. European Patent Laid-Open Application No. 97592 discloses to carry out the reaction in a solvent such as ethanol using $Rh_6(CO)_{16}$ as a catalyst with addition of 3,4,5,6,7,8-hexamethylphenanthroline under high temperature and high pressure e.g. 165° C. and CO 30 atm. As a reaction at high temperature (e.g., 80° C.) and under atmospheric pressure, "Journal of Molecular Catalysis", Vol. 12, No. 385 (1981) discloses to carry out the reaction in a solvent of 2-ethoxyethanol-water using $Rh_6(CO)_{16}$ as a catalyst with addition of various amines. As a reaction under room temperature and atmospheric pressure, "Tetrahedron Letters", Vol. 21, No. 27, 2603-2604 (1980) discloses to carry out the reaction in a mixed solution of 2-methoxyethanol-benzene-aqueous sodium hydroxide solution using a catalyst $Ru_3(CO)_{12}$ and a phase-transfer catalyst such as $(PhCH_2)Et_3N^+Cl^-$.

However, according to these methods, since catalytic activities are low and the reduction is difficult to proceed under moderate conditions, it is necessary to raise reaction temperature or enhance CO pressure. Furthermore, there is a problem in selectivity of reaction products under conditions of high temperature and high pressure. Under the moderate conditions of room temperature and atmospheric pressure, since catalytic activity is low, desired compounds are hardly obtained in high yields unless catalyst concentration is increased or reaction is conducted for a long time even with addition of phase-transfer catalysts.

SUMMARY OF THE INVENTION

An object of the present invention is to provide a process for producing an aromatic amine by reduction of an aromatic nitro compound under a $CO/H_2O$ system and moderate conditions using a catalyst higher in activity than conventional catalysts.

Another object of the present invention is to provide a process for producing an aromatic amine by catalytic reduction of aromatic nitro compounds using CO and water in high yield and with remarkably high selectivity.

That is, the present invention provides a process for producing an aromatic amine by reducing an aromatic nitro compound under a $CO/H_2O$ system using a catalyst comprising a rhodium compound, characterized by carrying out the reduction in the presence of an aqueous alkali solution.

The present invention further provides a process for producing an aromatic amine by reducing an aromatic nitro compound under a $CO/H_2O$ system using a catalyst comprising a rhodium compound or a ruthenium compound, characterized by carrying out the reduction with addition of at least one compound selected from the group consisting of amine compounds, diamine compounds, phosphine compounds, phosphite compounds and diphosphine compounds in the presence of an aqueous alkali solution.

DESCRIPTION OF THE INVENTION

The present invention will be explained in detail.

It is presumed that the reaction proceeds according to the following formula when, for example, nitrobenzene is used as aromatic nitro compounds.

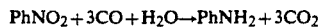

$$PhNO_2 + 3CO + H_2O \rightarrow PhNH_2 + 3CO_2$$

This reaction is characterized in that $CO/H_2O$ is used as a hydrogen source.

The aromatic nitro compound used in the present invention is a compound having at least one nitro group in an aromatic ring. The aromatic ring includes heterocyclic aromatic rings such as pyridine and quinoline in addition to hydrocarbon aromatic rings such as benzene, naphthalene and anthracene. Furthermore, these aromatic nitro compounds may have substituents such as an alkyl group, halogen, an amino group, a hydroxyl group, a carbonyl group, an alkoxy group, a cyano group and a sulfone group in addition to a nitro group. As aromatic nitro compounds normally used, mention may be made of, for example, nitrobenzene, o-nitrotoluene, p-nitrotoluene, 2-nitro-p-xylene, o-chloronitrobenzene, p-chloronitrobenzene, p-cyanonitrobenzene, o-nitroaniline, o-dinitrobenzene, p-nitroaniline, m-dinitrobenzene, 2,4-dinitrotoluene, o-nitrophenol, p-nitrophenol, o-nitroanisole, p-nitroanisole, α-nitronaphthalene, β-nitronaphthalene, 1-nitroanthraquinone, 2-nitroanthraquinone, 1,5-dinitroanthraquinone, 1,8-dinitroanthraquinone, 4-nitroimidazole, o-nitrobenzonitrile, p-nitrobenzonitrile, o-nitrobenzenesulfonic acid, p-nitrobenzenesulfonic acid, o-nitrobenzenesulfonamide, and p-nitrobenzenesulfonamide.

The catalyst used in the present invention is a rhodium compound or a ruthenium compound and is preferably a complex having carbonyl ligand or a compound capable of easily forming a carbonyl complex under reaction conditions. As examples of this catalyst, mention may be made of $Rh(CO)_2(acac)$, $[RhCl(COD)]_2$, $RhH(CO)(PPh_3)_2$, $Rh_4(CO)_{12}$, $Rh_6(CO)_{16}$, $RhCl(CO)(PPh_3)_2$, $Rh_2(OAc)_4$, $Rh(acac)_3$, $RhCl(PPh_3)_3$, $RhH(PPh_3)_3$, $RuH_2(PPh_3)_4$, $RuCl_2(PPh_3)_4$, $RuCl_2(CO)_2(PPh_3)_2$, $Ru_3(CO)_{12}$, $H_4Ru_4(CO)_{12}$, $Ru(acac)_3$, $Ru(CF_3COCH_2COCF_3)_3$, $RuH(OAc)(PPh_3)_3$, $RuHCl(PPh_3)_3$, and $[RuCl_2(COD)]n$. Among them, carbonyl complexes of rhodium or ruthenium are especially preferred.

In the present invention, excellent catalytic activity is exhibited by using an aqueous alkali solution. The aqueous alkali solution may be an aqueous solution of any of LiOH, NaOH, KOH, RbOH, and CsOH. Usually, an aqueous solution of NaOH is used. Alkali concentration is usually 0.1-10N, preferably 3-7N.

Reaction temperature is usually 0°-200° C. especially preferably 20°-150° C. and the reaction proceeds efficiently even at about room temperature (about 25° C.).

The reaction proceeds without a solvent, but use of a solvent is more preferred. The solvent includes, for example, alcohols such as 2-methoxyethanol, 2-propanol, methanol, and ethanol, hydrocarbons such as benzene, toluene, and xylene and glymes such as diethylene glycol dimethyl ether.

The pressure of CO used in the present invention is usually 1-100 atm or higher. The reaction of the present invention efficiently proceeds even under atmospheric pressure.

In the present invention, higher catalytic activity is exhibited by using catalyst systems comprising a rhodium compound or a ruthenium compound to which is added at least one compound selected from amine compounds, diamine compounds, phosphine compounds, phosphite compounds and diphosphine compounds.

The amine compounds used in the present invention include primary amines, secondary amines and tertiary amines. Examples thereof are imidazoles such as imidazole, N-methylimidazole, 2-methylimidazole, benzimidazole, 2-methylbenzimidazole, and N-methylbenzimidazole, pyridines such as 4,4-dimethylaminopyridine, pyridine, α-picoline, β-picoline, γ-picoline, 4-cyanopyridine, 2-cyanopyridine and 2-hydroxypyridine, pyrrolidine, piperidine, piperazine, pyrrole, triethylamine, trinormalpropylamine, trinormalbutylamine, N,N-dimethylbenzylamine, diisopropylamine, and 1-aminoanthraquinone. Among them, preferred are 2-methylbenzimidazole, triethylamine, trinormalbutylamine, 2-hydroxypyridine and N,N-dimethylbenzylamine.

The diamines used in the present invention are chelate amines which have two nitrogen atoms at 2,2'; 1,2 (including 2,3 and 9,10); 1,3; 1,4; 1,5; 1,8 or 1,10 positions and examples thereof are ethylenediamine, N,N,N',N'-tetramethylethylenediamine, N,N,N',N'-tetramethyl-1,3-propanediamine, N,N,N',N'-tetramethyl-1,4-butanediamine, o-phenylenediamine, 9,10-diaminophenanthrene, 2,3-naphthalenediamine, 1,8-naphthalenediamine, 1,8-bis(dimethylamino)naphthalene, 2-aminopyridine, α,α'-bipyridyl, 1,10-phenanthroline, and 3,4,7,8-tetramethyl-1,10-phenanthroline. Among them, preferred are aromatic diamines such as 9,10-diaminophenanthrene, o-phenylenediamine, 1,8-bis(dimethylamino)naphthalene and N,N,N',N'-teteramethyl-1,4-butanediamine.

The above amines or diamines are added in an amount of usually 0.01-200 mols, more preferably 0.01-20 mols per one mol of a catalyst metal atom.

The phosphines used in the present invention are represented by the formula: $PR^1R^2R^3$ (wherein $R^1$, $R^2$ and $R^3$ each represents an alkyl group of 1-8 carbon atoms, a cycloalkyl group of 6-8 carbon atoms or a phenyl group, with a proviso that all of $R^1$, $R^2$ and $R^3$ are not simultaneously phenyl groups). Examples are trialkylphosphines such as trimethylphosphine, triethylphosphine, tri-n-propylphosphine, triisopropylphosphine, tri-n-butylphosphine, tri-tert-butylphosphine and tri-cyclohexylphosphine, tertiary phosphines having phenyl group such as diphenylethylphosphine, diphenylmethylphosphine, diethylphenylphosphine and dimethylphenylphosphine, and tertiary phosphines having different alkyl groups or cycloalkyl groups such as ethyl-di-tert-butylphosphine. Preferred are diethylphenylphosphine and triethylphosphine.

The phosphites used in the present invention are represented by the formula: $P(OR)_3$ (wherein R represents an alkyl group of 1-5 carbon atoms or a phenyl group) and examples thereof are compounds where a hydrocarbon group and a phosphorus atom are bonded through an oxygen atom such as trimethylphosphite, triethylphosphite and triphenylphosphite. The phosphine or phosphite are added in an amount of 0.01-100 mols, more preferably 0.01-20 mols per one mol of a catalyst metal atom.

The diphosphines used in the present invention are chelate phosphines having two phosphorus atoms which are represented by the formula: $R_2P(CH_2)nPR_2$ (wherein R represents an alkyl group of 1-8 carbon atoms, a cycloalkyl group of 6-8 carbon atoms, a phenyl group or a tolyl group and n denotes an integer of 1-6) such as $Ph_2PCH_2PPh_2$, $Ph_2P(CH_2)_2PPh_2$, $Ph_2P(CH_2)_3PPh_2$, $Ph_2P(CH_2)_4PPh_2$, $Ph_2P(CH_2)_5PPh_2$, $nBu_2P(CH_2)_2PnBu_2$, $Et_2P(CH_2)_2PEt_2$, $Me_2PCH_2PMe_2$, $Me_2P(CH_2)_2PMe_2$, $(C_6H_{11})_2P(CH_2)_2P(C_6H_{11})_2$, and $(p-CH_3C_6H_4)_2P(CH_2)_2P(p-CH_3C_6H_4)_2$. Among them, preferred are $Ph_2PCH_2PPh_2$, $Ph_2P(CH_2)_2PPh_2$ and $Ph_2P(CH_2)_5PPh_2$. The diphosphine is added in an amount of usually 0.01-10 mols, preferably 0.01-4 mols per one mol of a catalyst metal atom.

In the present invention, when a rhodium compound is used as a catalyst, sufficiently superior catalytic activity is able to be exhibited with use of only an aqueous alkali solution and without addition of the above-mentioned amine compounds, diamine compounds, phosphine compounds, phosphite compounds and diphosphine compounds.

As explained in detail above, according to the present invention, catalytic activity is high and even under very moderate conditions such as room temperature and atmospheric pressure, catalytic activity conspicuously higher than that in conventional techniques and besides the objective aromatic amines are obtained selectively and in high yields. Thus, the present invention is remarkably economical.

The following nonlimiting examples will further explain the invention.

EXAMPLES 1-4

In Schlenk tubes of 50 ml each in capacity were introduced catalysts shown in Table 1 (0.02 mmol) (0.01 mmol in Example 4), 2-methoxyethanol (15 ml), a 5N aqueous sodium hydroxide solution (5 ml) and nitrobenzene (5 mmol) respectively and gas bags each of carbon monoxide (1 atm) was equipped at the ends of the Schlenk tubes, followed by stirring at 25° C. for 3 hours to allow the reactions proceed.

The reaction products were analyzed by gas chromatography and identification was carried out by comparison of retention time in gas chromatogram and by GC-MS.

The same analytical method was employed in the following examples and comparative examples.

As a result of the analysis, the reaction products comprised only aniline and no by-products were present.

The results are shown in Table 1.

The following total turnover number (TN) was used as an indicator for catalytic activity.

Total turnover number (TN) = amount of aromatic amine produced (mmol)/ amount of a catalyst metal atom (mg — atom).

EXAMPLE 5

$Rh_4(CO)_{12}$ (0.01 mmol), diethylene glycol dimethyl ether (30 ml), a 5N aqueous sodium hydroxide solution (10 ml) and 1-nitroanthraquinone (10.6 mmol) were introduced in a three-necked flask of 200 ml capacity and two gas bags of carbon monoxide (1 atm) were equipped at the end of the tube by a three-way cock and the content was stirred at 25° C. for 3 hours to allow the reaction proceed.

The reaction product comprised only 1-aminoanthraquinone and no by-products were present.

Results of the reaction are shown in Table 1.

COMPARATIVE EXAMPLE 1

Reaction was carried out in the same manner as in Example 1 except that an aqueous alkali solution was not used and $Rh_4(CO)_{12}$(0.02 mmol), 2-methhoxyethanol (5 ml) and water (1 ml) were used.

The reaction product comprised only aniline and no by-products were present. Results are shown in Table 1.

TABLE 1

|  | Catalyst | TN |
| --- | --- | --- |
| Example 1 | $Rh_4(CO)_{12}$ | 23 |
| Example 2 | $Rh(CO)_2(acac)$ | 37 |
| Example 3 | $[RhCl(COD)]_2$ | 30 |
| Example 4[1] | $Rh_6(CO)_{16}$ | 81 |
| Example 5 | $Rh_4(CO)_{12}$ | 93 |
| Comparative Example 1 | $Rh_4(CO)_{12}$ | 1 or less |

Note:
[1] Reaction time 5 hours, yield 87%

EXAMPLES 6-16

In Schlenk tubes of 50 ml each in capacity were introduced $Rh(CO)_2(acac)$ (0.02 mmol in Example 6 and 0.005 mmol in other Examples), diethylene glycol dimethyl ether (7.5 ml), a 5N aqueous sodium hydroxide solution (2.5 ml), phosphine or phosphite shown in Table 2 in an iquimolar amount with the catalyst (0.005 mmol) and nitrobenzene (5 mmol) and a gas bag each of carbon monoxide (1 atm) was equipped at the ends of the tubes and reactions were allowed to proceed for 2 hours at 25° C. with stirring.

The reaction product comprised only aniline and no by-products were present.

Results of the reaction are shown in Table 2.

TABLE 2

|  | Phosphine or phosphite | TN |
| --- | --- | --- |
| Example 6 | — | 5 |
| Example 7 | $PEtPh_2$ | 14 |
| Example 8 | $PEt_2Ph$ | 116 |
| Example 9 | $PEt_3$ | 241 |
| Example 10 | $PMe_3$ | 91 |
| Example 11 | $PCy_3$ | 35 |
| Example 12 | $P(i-C_3H_7)_3$ | 27 |
| Example 13 | $P(OEt)_3$ | 21 |
| Example 14 | $P(OPh)_3$ | 39 |
| Example 15 | $P(t-Bu)_3$ | 15 |
| Example 16 | $PEt(t-Bu)_2$ | 28 |
| Example 17 | $PEt_3$ | 22 |

EXAMPLE 17

Reaction was carried out in the same manner as in Example 7 except that $[RuCl_2(COD)]n$ (manufactured by Kanto Chemical Co.) (0.01 mmol Ru), triethylphosphine (0.01 mmol), 2-methoxyethanol (15 ml) and a 5N aqueous sodium hydroxide solution (5 ml) were used.

The reaction product comprised only aniline and no by-products were present.

Results of the reaction are shown in Table 2.

EXAMPLES 18-21

Reactions were carried out in the same manner as in Example 7 except that phosphine was used in the amounts as shown in Table 3.

The reaction products comprised only aniline and no by-products were present.

Results of the reactions are shown in Table 3.

TABLE 3

|  | Phosphine | Molar ratio[1] | TN |
| --- | --- | --- | --- |
| Example 18 | $PEt_2Ph$ | 2 | 75 |
| Example 19 | $PEt_3$ | 2 | 154 |
| Example 20 | $PEt_3$ | 5 | 140 |
| Example 21 | $PEt_3$ | 10 | 102 |

Note [1]: Amount of phosphine (mmol)/amount of a catalyst metal atom (mg-atm)

EXAMPLES 22-27

Reactions were carried out under the same conditions as in Example 7 except that amount of diethylene glycol dimethyl ether was changed to 15 ml and amount of a 5N aqueous sodium hydroxide solution was changed to 5 ml and phosphines or nitro compounds (5 mmol) as shown in Table 4 were used and reaction temperatures and reaction times as shown in Table 4 were employed.

The reaction products comprised only the desired compound and no by-products were present.

Results of the reaction are shown in Table 4.

TABLE 4

|  | Nitro-compound | Phosphine | Reaction temperature (°C.) | Reaction time (Hr) | TN | Yield (%) |
| --- | --- | --- | --- | --- | --- | --- |
| Example 22 | Nitrobenzene | $PEtPh_2$ | 50 | 2 | 52 | 5 |
| Example 23 | Nitrobenzene | $PEt_2Ph$ | 50 | 2 | 609 | 59 |
| Example 24 | Nitrobenzene | $PEt_3$ | 50 | 2.5 | 758 | 70 |
| Example 25 | Nitrobenzene | $PEt_3$ | 25 | 12 | 237 | 95 |
| Example 26 | p-Nitrotoluene | $PEt_3$ | 25 | 12 | 192 | 77 |
| Example 27 | p-Chloronitro- | $PEt_3$ | 25 | 12 | >250 | 100 |

TABLE 4-continued

| Nitro-compound | Phosphine | Reaction temperature (°C.) | Reaction time (Hr) | TN | Yield (%) |
|---|---|---|---|---|---|
| benzene | | | | | |

EXAMPLE 28–36

Reactions were carried out under the same conditions as in Example 1 except that catalysts (0.02 mmol with the exception of 0.005 in Example 29 and 0.01 mmol in Example 36) and diphosphines as shown in Table 5 were used.

In Example 29, the reaction was carried out using diethylene glycol dimethyl ether (7.5 ml) and a 5N aqueous sodium hydroxide solution (2.5 ml).

Reaction products comprised only aniline and no by-products were present.

Results of the reaction are shown in Table 5.

COMPARATIVE EXAMPLES 2–4

Reactions were carried out under the same conditions as in Example 1 except that catalysts (0.02 mmol) and phosphines as shown in Table 5 were used. Phosphine was not added in Comparative Example 2.

Reaction products comprised only aniline and no by-products were present.

Results of the reactions are shown in Table 5.

TABLE 5

| | Catalyst | Phosphine or diphosphine[1] | Molar ratio[2] | TN |
|---|---|---|---|---|
| Example 28 | $Rh(CO)_2(acac)$ | dppe | 1.0 | 51 |
| Example 29 | $Rh(CO)_2(acac)$ | dmpe | 1.0 | 45 |
| Example 30 | $Rh_4(CO)_{12}$ | dppm | 0.09 | 32 |
| Example 31 | $Rh_4(CO)_{12}$ | dppm | 0.25 | 50 |
| Example 32 | $Rh_4(CO)_{12}$ | dppe | 0.25 | 39 |
| Example 33 | $Rh_4(CO)_{12}$ | dppp | 0.25 | 47 |
| Example 34 | $Ru_3(CO)_{12}$ | dppe | 0.33 | 27 |
| Example 35 | $Ru_3(CO)_{12}$ | dppe | 0.50 | 32 |
| Example 36 | $Ru_3(CO)_{12}$ | dppe | 0.50 | 26 |
| Comparative Example 2 | $Ru_3(CO)_{12}$ | — | — | 17 |
| Comparative Example 3 | $Ru_3(CO)_{12}$ | $PPh_3$ | 0.3 | 14 |
| Comparative Example 4 | $Rh_4(CO)_{12}$ | $PPh_3$ | 0.25 | 12 |
| Example 4 | | | | |

Notes
[1]dppm: Bis(diphenylphosphino)methane
dppe: 1,2-Bis(diphenylphosphino)ethane
dppp: 1,5-Bis(diphenylphosphino)pentane
dmpe: 1,2-Bis(dimethylphosphino)ethane
[2]Amount of phosphine or diphosphine (mmol)/amount of a catalyst metal atom (mg-atm)

EXAMPLES 37–46

In Schlenk tubes of 50 ml each capacity were introduced catalysts shown in Table 6 (0.02 mmol). 2-methoxyethanol (15 ml), a 5N aqueous sodium hydroxide solution (5 ml), 1,2-bis(diphenylphosphino)ethane in the amount as shown in Table 6 and nitro compounds as shown in Table 6 (5 mmol) and gas bag each of carbon monoxide (1 atm) was equipped at the ends of the Schlenk tubes and reactions were allowed to proceed by stirring at 25° C. for a reaction time as shown in Table 6.

The reaction products comprised only the objective compound and no by-products were present.

Results of the reaction are shown in Table 6.

TABLE 6

| | Catalyst | Molar ratio[1] | Nitro compound | Reaction time (Hr) | Product | TN | Yield (%) |
|---|---|---|---|---|---|---|---|
| Example 37 | $Rh_4(CO)_{12}$ | 0.25 | Nitrobenzene | 1.5 | Aniline | 27 | 44 |
| Example 38 | $Rh_4(CO)_{12}$ | 0.25 | o-Chloronitrobenzene | 1.5 | o-Chloroaniline | 52 | 84 |
| Example 39 | $Rh_4(CO)_{12}$ | 0.25 | o-Nitroaniline | 1.5 | o-Phenylenediamine | 48 | 76 |
| Example 40 | $Rh_4(CO)_{12}$ | 0.25 | p-Nitroaniline | 1.5 | p-Phenylenediamine | >63 | 100 |
| Example 41 | $Rh_4(CO)_{12}$ | 0.25 | p-Nitroanisole | 1.5 | p-Anisidine | 35 | 56 |
| Example 42 | $Rh_4(CO)_{12}$ | 0.25 | p-Nitrotoluene | 1.5 | p-Toluidine | 32 | 51 |
| Example 43 | $Rh_4(CO)_{12}$ | 0.25 | p-Chloronitrobenzene | 1.5 | p-Chloroaniline | 40 | 63 |
| Example 44 | $Ru_3(CO)_{12}$ | 0.50 | p-Chloronitrobenzene | 3 | p-Chloroaniline | 63 | 76 |
| Example 45 | $Ru_3(CO)_{12}$ | 0.50 | p-Nitrotoluene | 3 | p-Toluidine | 23 | 28 |
| Example 46 | $Ru_3(CO)_{12}$ | 0.50 | p-Nitroanisole | 3 | p-Anisidine | 24 | 29 |

Note
[1]Amount of diphosphine (mmol)/amount of a catalyst metal atom (mg-atm)

EXAMPLES 47–66

Reactions were carried out under the same conditions as in Example 2 except that amine or diamine as shown in Table 7 was used. In Example 62, amount of $Rh(CO)_2(acac)$ was 0.01 mmol.

Reaction products comprised only aniline and no by-products were present.

Results of the reaction are shown in Table 7.

TABLE 7

| | Amine or diamine | Molar ratio[1] | TN |
|---|---|---|---|
| Example 47 | N-methylimidazole | 3 | 52 |
| Example 48 | Pyridine | 3 | 61 |
| Example 49 | Pyrrolidine | 3 | 54 |

TABLE 7-continued

| | Amine or diamine | Molar ratio[1] | TN |
|---|---|---|---|
| Example 50 | Triethylamine | 3 | 66 |
| Example 51 | 2-Aminopyridine | 1.5 | 60 |
| Example 52 | Ethylenediamine | 1.5 | 52 |
| Example 53 | N,N,N',N'-tetramethylethylenediamine | 1.5 | 68 |
| Example 54 | N,N,N',N'-tetramethyl-1,3-propanediamine | 1.5 | 62 |
| Example 55 | o-Phenylenediamine | 1.5 | 155 |
| Example 56 | 2,3-Naphthalenediamine | 1.5 | 99 |
| Example 57 | 9,10-Diaminophenanthrene | 1.0 | 118 |
| Example 58 | 9,10-Diaminophenanthrene | 1.5 | 122 |
| Example 59 | 9,10-Diaminophenanthrene | 4.0 | 98 |
| Example 60[2] | 9,10-Diaminophenanthrene | 1.5 | 241 |
| Example 61[3] | 9,10-Diaminophenanthrene | 1.5 | 72 |
| Example 62[4] | 9,10-Diaminophenanthrene | 1.5 | 172 |
| Example 63 | 1,8-Naphthalenediamine | 1.5 | 68 |
| Example 64 | α,α'-bipyridyl | 1.5 | 60 |
| Example 65 | 3,4,7,8-tetramethyl-1,10-phenanthroline | 1.5 | 57 |
| Example 66 | N,N,N',N'-tetramethyl-1,4-butanediamine | 1.5 | 60 |

Notes:
[1] Amount of amine or diamine (mmol)/amount of a catalyst metal atom (mg-atm)
[2] 12 hours, yield 95%
[3] 1 hour
[4] Ph(CO)₂(acac) (0.01 mmol)

EXAMPLES 67–72

Reactions were carried out under the same conditions as in Example 6 except that amine or diamine shown in Table 8 and Rh₆(CO)₁₆ (0.001 mmol) were used.

Reaction products comprised only aniline and no by-products were present.

Results of the reaction are shown in Table 8.

TABLE 8

| | Amine or diamine | Molar ratio[1] | TN |
|---|---|---|---|
| Example 67 | triethylamine | 3 | 47 |
| Example 68 | trinormalpropylamine | 3 | 43 |
| Example 69 | diisopropylamine | 3 | 28 |
| Example 70 | 4-cyanopyridine | 3 | 30 |
| Example 71 | piperadine | 3 | 30 |
| Example 72 | N,N,N',N'-tetramethyl-1,4-butanediamine | 1 | 27 |

Notes:
[1] Amount of amine or diamine (mmol)/amount of a catalyst metal atom (mg-atm)

EXAMPLES 73–92

Reactions were carried out for 1 hour under the same conditions as in Example 4 except that amine or diamine shown in Table 9, p-nitrotoluene or p-nitroanisole (5 mmol) as aromatic nitro compounds were used in the presence of Rh₆(CO)₁₆ (0.001 mmol).

Reaction products comprised only p-toluidine from p-nitrotoluene and p-anisidine from p-nitroanisole and no by-products were present.

Results of the reaction are shown in Table 9.

TABLE 9

| | Amine or diamine | Molar ratio[1] | Nitro compounds | TN |
|---|---|---|---|---|
| Example 73 | triethylamine | 3 | p-nitrotoluene | 79 |
| Example 74 | trinormalbutylamine | 3 | p-nitrotoluene | 168 |
| Example 75 | N,N,N',N'-tetramethyl-1,4-butanediamine | 1 | p-nitrotoluene | 175 |
| Example 76 | pyrrolidine | 3 | p-nitrotoluene | 80 |
| Example 77 | pyrrole | 3 | p-nitrotoluene | 88 |
| Example 78 | piperidine | 3 | p-nitrotoluene | 98 |
| Example 79 | piperidine | 3 | p-nitrotoluene | 101 |
| Example 80 | imidazole | 3 | p-nitrotoluene | 107 |
| Example 81 | benzimidazole | 3 | p-nitrotoluene | 99 |
| Example 82 | o-phenanthroline | 1 | p-nitrotoluene | 123 |
| Example 83 | 3,4,7,8-tetramethyl-1,10-phenanthroline | 1 | p-nitrotoluene | 93 |
| Example 84 | N,N-dimethylbenzylamine | 3 | p-nitrotoluene | 203 |
| Example 85 | ethylenediamine | 1 | p-nitroanisole | 138 |
| Example 86 | 4-cyanopyridine | 3 | p-nitroanisole | 163 |
| Example 87 | 4,4-dimethylaminopyridine | 3 | p-nitroanisole | 130 |
| Example 88 | 2-hydroxypyridine | 3 | p-nitroanisole | 294 |
| Example 89 | 1,8-bis(dimethylamino)naphthalene | 1.5 | p-nitroanisole | 296 |
| Example 90 | N,N-dimethylbenzylamine | 3 | p-nitroanisole | 225 |
| Example 91 | trinormalbutylamine | 3 | p-nitroanisole | 236 |
| Example 92 | N,N,N',N'-tetramethyl-1,4-butanediamine | 1 | p-nitroanisole | 173 |

[1] Amount of amine or diamine (mmol)/amount of a catalyst metal atom (mg-atm)

EXAMPLES 93–106

Reactions were carried out under the same conditions as in Example 1 except that amine or diamine as shown in Table 10 and nitrobenzene (10 mmol) and Ru₃(CO)₁₂ (0.02 mmol) were used.

Reaction products comprised only aniline and no by-products were present.

Results of the reaction are shown in Table 10.

EXAMPLES 107–114 AND COMPARATIVE EXAMPLE 5

Reactions were carried out in the same manner as in Example 58 except that solvents and bases as shown in Table 11 were used.

Reaction products comprised only aniline and no by-products were present.

Results of the reaction are shown in Table 11.

TABLE 10

| | Amine or diamine | Molar ratio[1] | TN |
|---|---|---|---|
| Example 93 | N,N,N',N'-tetramethyl-ethylenediamine | 1.5 | 26 |
| Example 94 | N,N,N',N'-tetramethyl-1,3-propanediamine | 1.5 | 30 |
| Example 95 | N,N,N',N'-tetramethyl-1,4-butanediamine | 1.5 | 28 |
| Example 96 | 2,3-Naphthalenediamine | 1.5 | 26 |
| Example 97 | 9,10-Diaminophenanthrene | 1.5 | 31 |
| Example 98 | 3,4,7,8-Tetramethyl-1,10-phenanthroline | 1.5 | 29 |
| Example 99 | Imidazole | 3 | 27 |
| Example 100 | N-methylimidazole | 3 | 27 |
| Example 101 | 2-Methylimidazole | 3 | 26 |
| Example 102 | Benzimidazole | 3 | 26 |
| Example 103 | 2-Methylbenzimidazole | 3 | 37 |
| Example 104 | Pyridine | 3 | 37 |
| Example 105 | 4,4-Dimethylaminopyridine | 3 | 26 |

TABLE 10-continued

|  | Amine or diamine | Molar ratio[1] | TN |
|---|---|---|---|
| Example 106 | Triethylamine | 3 | 39 |

Note
[1] Amount of amine or diamine (mmol)/amount of a catalyst metal atom (mg-atm)

TABLE 11

|  | Solvent (ml) | | Base condition | | TN |
|---|---|---|---|---|---|
| Example 107 | 2-Methoxyethanol | 15 | 1.5N—NaOH | 5 ml | 64 |
| Example 108 | 2-Methoxyethanol | 15 | 3N—NaOH | 5 ml | 94 |
| Example 109 | 2-Methoxyethanol | 15 | 5N—NaOH | 2.5 ml | 78 |
| Example 110 | 2-Methoxyethanol | 8 | 5N—NaOH | 5 ml | 79 |
| Example 111 | 2-Methoxyethanol | 30 | 5N—NaOH | 5 ml | 118 |
| Example 112 | Ethanol | 15 | 5N—NaOH | 5 ml | 51 |
| Example 113 | 2-Propanol | 15 | 5N—NaOH | 5 ml | 69 |
| Example 114 | Toluene | 15 | 5N—NaOH | 5 ml | 55 |
| Comparative Example 5 | 2-Methoxyethanol | 15 | $H_2O$ | 5 ml | 25 |

EXAMPLES 115-120

Reactions were carried out under the same conditions as in Example 1 except that $Rh_4(CO)_{12}$ as shown in Table 12 and 9,10-diaminophenanthrene were used.

Reaction products comprised only aniline and no by-products were present.

Results of the reaction are shown in Table 12.

COMPARATIVE EXAMPLES 6-8

Reactions were carried out under the same conditions as in Example 1 except that water (5 ml) in place of the 5N aqueous sodium hydroxide solution, N,N,N',N'-tetramethylethylenediamine and $Rh_4(CO)_{12}$ of the concentration as shown in Table 12 were used. In comparative Example 7, reaction temperature was 70° C. and in Comparative Example 8, reaction temperature was 70° C. and CO pressure was 50 kg/cm².

Reaction products comprised only aniline and no by-products were present.

Results of the reaction are shown in Table 12.

TABLE 12

|  | $Rh_4(CO)_{12}$(mmol) | Molar ratio[1] | TN |
|---|---|---|---|
| Example 115 | 0.02 | 0.06 | 28 |
| Example 116 | 0.02 | 1.1 | 50 |
| Example 117[2] | 0.02 | 2.3 | 56 |

TABLE 12-continued

|  | $Rh_4(CO)_{12}$(mmol) | Molar ratio[1] | TN |
|---|---|---|---|
| Example 118[3] | 0.005 | 1.5 | 65 |
| Example 119[4] | 0.005 | 1.5 | 125 |
| Example 120[5] | 0.005 | 1.5 | 284 |
| Comparative Example 6 | 0.02 | 75 | 1 or less |
| Comparative Example 7[6] | 0.02 | 75 | 13 |
| Comparative Example 8[7] | 0.02 | 75 | 35 |

Notes
[1] Amount of diamine (mmol)/amount of a catalyst metal atom (mg-atm)
[2] Yield 90%
[3]-[5] Nitrobenzene 10 mmol
[3] Reaction time 1 hour
[5] Reaction time 9 hours
[6] Reaction temperature 70° C.
[7] Reaction temperature 70° C., CO pressure 50 kg/cm²

EXAMPLES 121-125

Reactions were carried out under the same conditions as in Example 5 except that amines as shown in Table 13 were used.

Reaction products comprised only 1-aminoanthraquinone and no by-products were present.

Results of the reaction are shown in Table 13.

TABLE 13

|  | Amine | Molar ratio[1] | TN |
|---|---|---|---|
| Example 121 | Triethylamine | 3 | 139 |
| Example 122 | Triethylamine | 10 | 114 |
| Example 123 | 4,4'-Dimethylaminopyridine | 3 | 132 |
| Example 124 | 1-Aminoanthraquinone | 3 | 117 |
| Example 125 | 9,10-Diaminophenanthrene | 1.5 | 105 |

[1] Amount of diamine (mmol)/amount of a catalyst metal atom (mg-atm)

EXAMPLES 126-146

In Schlenk tubes of 50 ml each were charged catalysts shown in Table 14, amines or diamines shown in Table 14, 2-methoxyethanol (15 ml), a 5N aqueous sodium hydroxide solution (5 ml), and nitro compounds shown in Table 14 (5 mmol except 5.3 mmol in Examples 145 and 146) and a gas bag each of carbon monoxide (1 atm) was equipped at the ends of the Schlenk tubes and reactions were allowed to proceed at 25° C. for periods as shown in Table 14 with stirring.

Reaction products comprised only the desired product and no by-products were present.

Results of reaction are shown in Table 14.

TABLE 14

|  | Catalyst | (mmol) | Amine or diamine | Molar ratio[1] | Nitro compound | Reaction time (Hr) | Product | TN | Yield (%) |
|---|---|---|---|---|---|---|---|---|---|
| Example 126 | $Rh_4(CO)_{12}$ | 0.02 | 9,10-Diaminophenanthrene | 1.5 | Nitrobenzene | 1.5 | Aniline | 40 | 63 |
| Example 127 | $Rh_4(CO)_{12}$ | 0.02 | 9,10-Diaminophenanthrene | 1.5 | o-Chloronitrobenzene | 1.5 | o-Chloroaniline | 47 | 76 |
| Example 128 | $Rh_4(CO)_{12}$ | 0.02 | 9,10-Diaminophenanthrene | 1.5 | o-Chloronitrobenzene | 10 | o-Chloroaniline | >63 | 100 |
| Example 129 | $Rh(CO)_2(acac)$ | 0.04 | 9,10-Diaminophenanthrene | 1.5 | o-Chloronitrobenzene | 20 | o-Chloroaniline | 110 | 88 |
| Example 130 | $Rh_4(CO)_{12}$ | 0.02 | 9,10-Diaminophenanthrene | 1.5 | p-Chloronitrobenzene | 1.5 | p-Chloroaniline | 54 | 87 |
| Example 131 | $Ru_3(CO)_{12}$ | 0.005 | Triethylamine | 3 | p-Chloronitrobenzene | 14 | p-Chloroaniline | 263 | 79 |
| Example 132 | $Rh(CO)_2(acac)$ | 0.005 | 9,10-Diaminophenanthrene | 1.5 | p-Chloronitrobenzene | 0.5 | p-Chloroaniline | 787 | 79 |
| Example 133 | $Rh_4(CO)_{12}$ | 0.02 | 9,10-Diaminophenanthrene | 1.5 | o-Nitroaniline | 1.5 | o-Phenylenediamine | 58 | 93 |

TABLE 14-continued

| | Catalyst (mmol) | | Amine or diamine | Molar ratio[1] | Nitro compound | Reaction time (Hr) | Product | TN | Yield (%) |
|---|---|---|---|---|---|---|---|---|---|
| Example 134 | Rh$_4$(CO)$_{12}$ | 0.02 | 9,10-Diaminophenanthrene | 1.5 | o-Nitroaniline | 10 | o-Phenylenediamine | 60 | 96 |
| Example 135 | Rh(CO)$_2$(acac) | 0.04 | 9,10-Diaminophenanthrene | 1.5 | o-Nitroaniline | 20 | o-Phenylenediamine | 108 | 86 |
| Example 136 | Rh$_4$(CO)$_{12}$ | 0.02 | 9,10-Diaminophenanthrene | 1.5 | p-Nitroaniline | 1.5 | p-Phenylenediamine | >63 | 100 |
| Example 137 | Ru$_3$(CO)$_{12}$ | 0.005 | Triethylamine | 3 | p-Nitroaniline | 14 | p-Phenylenediamine | >333 | 100 |
| Example 138 | Rh(CO)$_2$(acac) | 0.005 | 9,10-Diaminophenanthrene | 1.5 | p-Nitroaniline | 0.5 | p-Phenylenediamine | >1000 | 100 |
| Example 139 | Rh$_4$(CO)$_{12}$ | 0.02 | 9,10-Diaminophenanthrene | 1.5 | p-Nitroanisole | 1.5 | p-Anisidine | 44 | 70 |
| Example 140 | Rh$_4$(CO)$_{12}$ | 0.02 | 9,10-Diaminophenanthrene | 1.5 | p-Nitroanisole | 10 | p-Anisidine | 60 | 95 |
| Example 141 | Rh$_4$(CO)$_{12}$ | 0.02 | 9,10-Diaminophenanthrene | 1.5 | p-Nitrotoluene | 1.5 | p-Toluidine | 44 | 71 |
| Example 142 | Rh$_4$(CO)$_{12}$ | 0.02 | 9,10-Diaminophenanthrene | 1.5 | p-Nitrotoluene | 10 | p-Toluidine | 57 | 91 |
| Example 143 | Rh(CO)$_2$(acac) | 0.04 | 9,10-Diaminophenanthrene | 1.5 | p-Nitrotoluene | 20 | p-Toluidine | 101 | 81 |
| Example 144 | Rh$_4$(CO)$_{12}$ | 0.02 | 9,10-Diaminophenanthrene | 1.5 | p-Cyanonitrobenzene | 10 | p-Cyanoaniline | >63 | 100 |
| Example 145[2] | Rh$_4$(CO)$_{12}$ | 0.02 | 9,10-Diaminophenanthrene | 1.5 | 1-Nitroanthraquinone | 12 | 1-Aminoanthraquinone | >65 | 99 |
| Example 146[2] | Ru$_3$(CO)$_{12}$ | 0.02 | Triethylene | 3 | 1-Nitroanthraquinone | 14 | 1-Aminoanthraquinone | >87 | 98 |

Note
[1] AMount of amine or diamine (mmol)/amount of catalyst metal atom (mg-atm)
[2] 1-Nitroanthraquinone (5.3 mmol)

We claim:

1. A process for producing an aromatic amine which comprises reducing an aromatic nitro compound under a CO/H$_2$O system in the presence of a catalyst comprising a rhodium compound wherein the reduction is carried out in the presence of an aqueous alkali solution which is an aqueous solution of LiOH, NaOH, KOH, RbOH or CsOH.

2. A process for producing an aromatic amine which comprises reducing an aromatic nitro compound under a CO/H$_2$O system in the presence of a catalyst comprising a rhodium compound or a ruthenium compound wherein the reduction is carried out in the presence of an aqueous alkali solution with addition of at least one compound selected from the group consisting of amine compounds, diamine compounds, phosphine compounds, phosphite compounds and diphosphine compounds, wherein the aqueous alkali solution is an aqueous solution of LiOH, NaOH, KOH, RbOH or CsOH.

3. A process according to claim 1 or 2, wherein the rhodium compound is Rh(CO)$_2$(acac), [RhCl(COD)]$_2$, Rd$_4$(CO)$_{12}$ or Rh$_6$(CO)$_{16}$.

4. A process according to claim 2, wherein the ruthenium compound is Ru$_3$(CO)$_{12}$ or [RuCl$_2$(COD)]n.

5. A process according to claim 2, wherein the amine compound is added and is a primary amine, a secondary amine or a tertiary amine.

6. A process according to claim 5, wherein the amine compound is a primary amine which is 1-aminoanthraquinone.

7. A process according to claim 5, wherein the amine compound is a secondary amine which is imidazole, 2-methylimidazole, benzimidazole, pyrrolidine, diisopropylamine or pyrrole.

8. A process according to claim 5, wherein the tertiary amine is added and is triethylamine, tri-n-propylamine, tri-n-butylamine, N,N-dimethylbenzylamine, N-methylimidazole, 4,4-dimethylaminopyridine, pyridine, 4-cyanopyridine, α-picoline, β-picoline, γ-picoline or 2-hydroxypyrindine.

9. A process according to claim 5, wherein the amine compound is 2-methylbenzimidazole, triethylamine, trinormalbutylamine, 2-hydroxypyridine or N,N-dimethylbenzylamine.

10. A process according to claim 2, wherein the diamine compound is added and is a chelate amine which has two nitrogen atoms at the 2,2', 1,2, 1,3, 1,4, 1,5, 1,8, or 1,10 positions.

11. A process according to claim 10, wherein the diamine compound is ethylenediamine, N,N,N', N'-tetramethylethylenediamine, N,N,N', N'-tetramethyl-1,3-propanediamine, N,N,N',N'-tetramethyl-1,4-butanediamine, 1,8-bis(dimethylamino)naphthalene, o-phenylenediamine, 9,10-diaminophenanthrene, 2,3-naphthalenediamine, 1,8-naphthalenediamine, 2-aminopyridine, α, α'-bipyridyl or 3,4,7,8-tetramethyl-1,10-phenanthroline.

12. A process according to claim 11, wherein the diamine compound is 9,10-diaminophenanthrene, o-phenylenediamine, 1,8-bis(dimethylamino)naphthalene or N,N,N',N'-tetramethyl-1,4-butanediamine.

13. A process according to claim 2, wherein the phosphine compound is added and is represented by the formula: PR$^1$R$^2$R$^3$ wherein R$^1$, R$^2$ and R$^3$ each represents an alkyl group of 1–8 carbon atoms, a cycloalkyl group of 6–8 carbon atoms or a phenyl group with a proviso that all of R$^1$, R$^2$ and R$^3$ are not simultaneously phenyl groups.

14. A process according to claim 13, wherein the phosphine compound is trimethylphosphine, triethylphosphine, triisopropylphosphine, tri-tert-butylphosphine, tricyclohexylphosphine, diphenylethylphosphine, diethylphenylphosphine or ethyl-di-tert-butylphosphine.

15. A process according to claim 14, wherein the phosphine compound is diethylphenylphosphine or triethylphosphine.

16. A process according to claim 2, wherein the phosphite compound is added and is represented by the formula: $P(OR)_3$ wherein R represents and alkyl group of 1-5 carbon atoms or a phenyl group.

17. A process according to claim 16, wherein the phosphite compound is triethylphosphite or triphenylphosphite.

18. A process according to claim 2, wherein the diphosphine compound is added and is represented by the formula: $R_2P(CH_2)nPR_2$ wherein R represents an alkyl group of 1-8 carbon atoms, a cycloalkyl group of 6-8 carbon atoms, a phenyl group or a tolyl group and n represents an integer of 1-6.

19. A process according to claim 18, wherein the diphosphine compound is bis(diphenylphosphino) methane, 1,2-bis(diphenylphosphino)ethane, 1,2-bis(-dimethylphosphino)ethane or 1,5-bis(diphenylphosphino)pentane.

20. A process according to claim 19, wherein the diphosphine compound is bis(diphenylphosphino)methane, 1,2-bis(diphenylphosphino)ethane or 1,5-bis(diphenylphosphino)pentane.

21. A process according to claim 2, wherein the amine compound or the diamine compound is added in an amount of 0.01-200 mols per one mol of the catalyst metal atom.

22. A process according to claim 2, wherein the amine compound or the diamine compound is added in an amount of 0.01-20 mols per one mol of the catalyst metal atom.

23. A process according to claim 2, wherein the phosphine compound or the phosphite compound is added in an amount of 0.01-100 mols per one mol of the catalyst metal atom.

24. A process according to claim 2, wherein the phosphine compound or the phosphite compound is added in an amount of 0.01-20 mols per one mol of the catalyst metal atom.

25. A process according to claim 2, wherein the diphosphine compound is added in an amount of 0.01-10 mols per one mol of the catalyst metal atom.

26. A process according to claim 2, wherein the diphosphine compound is added in an amount of 0.01-4 mols per one mol of the catalyst metal atom.

27. A process according to claim 1 or 2, wherein the aqueous alkali solution is aqueous sodium hydroxide solution.

28. A process according to claim 1 or 2, wherein reaction temperature is 20°-150° C. and CO pressure is 1-100 atm.

29. A process according to claim 1 or 2, wherein reaction temperature is 25° C. and CO pressure is 1 atm.

30. A process according to claim 1, wherein the alkali concentration of the aqueous solution is 0.1-10N.

31. A process according to claim 2, wherein the alkali concentration of the aqueous solution is 0.1-10N.

32. A process according to claim 1, wherein the alkali concentration of the aqueous solution is 3-7N.

33. A process according to claim 2, wherein the alkali concentration of the aqueous solution is 3-7N.

34. A process according to claim 1, wherein the process is conducted in the presence of a solvent selected from the group consisting of alcohols, hydrocarbons and glymes.

35. A process according to claim 2, wherein the process is conducted in the presence of a solvent selected from the group consisting of alcohols, hydrocarbons and glymes.

* * * * *